United States Patent
Lanigan et al.

Patent Number: 5,547,462
Date of Patent: Aug. 20, 1996

[54] BACK BRACE

[76] Inventors: William T. Lanigan, 50 Vine Rd., Larchmont, N.Y. 10538; Robert Carra, 8 Renee Rd., Syosset, N.Y. 11791

[21] Appl. No.: 528,133

[22] Filed: Sep. 14, 1995

[51] Int. Cl.⁶ .................... A61F 5/00; A61F 5/37
[52] U.S. Cl. ................................ 602/19; 128/876
[58] Field of Search .................. 128/845, 846, 128/869, 874, 875, 876; 602/5, 19; 2/311, 312, 338

[56] References Cited

U.S. PATENT DOCUMENTS

| | | | |
|---|---|---|---|
| 2,453,370 | 11/1948 | Hittenberger | 602/19 |
| 2,813,526 | 11/1957 | Beebe | 602/19 |
| 4,696,241 | 9/1987 | Tyo | 602/19 |
| 5,036,864 | 8/1991 | Yewer | 602/19 |

*Primary Examiner*—Michael A. Brown
*Attorney, Agent, or Firm*—Myron Amer, P.C.

[57] ABSTRACT

A back brace with front and back panels supported on a waist-encircling belt which during tightening to empower the back panel to impart pressure against the user's back also urges the front panel in ascending movement to supplement the back panel-imparted pressure.

1 Claim, 2 Drawing Sheets

BACK BRACE

The present invention relates generally to a back brace of a type which in use is worn about the waist for applying, what is intended as pain-relieving, pressure against the user's sacrum, and more particularly to a construction and operating mode in such back brace which facilitates the generating of the noted pressure.

BACKGROUND OF THE INVENTION

1. Field of the Invention

Back braces for applying pressure and/or support to the back of the user are, of course, already well known, being in many instances characterized by body-encircling configurations laced, belted, or otherwise secured in place. In all such known back braces the body-encircling use position is also unavoidably restrictive of body movement, thereby contributing to discomfort as well as imposing limitations on use to non-working circumstances and the like.

2. Description of the Prior Art

Nevertheless, a prior art back brace sufficiently pertinent to be noted is that described and illustrated in U.S. Pat. No. 5,111,806 issued to Travis for "Support Belt with Color Indicator" on May 12, 1992. The discomfort and body movement restriction using the Travis support belt can arguably be said to be nominal, but likewise it can be said that there is correspondingly only nominal pressure generated for application against the user's sacrum resulting from the tightening of the belt about the user's waist, i.e. a direct one-to-one relation between the extent of belt tightening and the extent of pressure exerted.

SUMMARY OF THE INVENTION

Broadly, it is an object of the present invention to provide a back brace having a belt-tightening mode, but overcoming the foregoing and other shortcomings of the prior art.

More particularly, it is an object to generate pain-relieving pressure in the sacrum area not only of an extent related to the degree of belt-tightening, but also as supplemented by ascending movements in the back brace components caused by said belt-tightening, all as will be better understood as the description proceeds.

BRIEF DESCRIPTION OF THE DRAWING

The description of the invention which follows, together with the accompanying drawings should not be construed as limiting the invention to the example shown and described, because those skilled in the art to which this invention appertains will be able to devise other forms thereof within the ambit of the appended claims.

DESCRIPTION OF THE PREFERRED EMBODIMENT

Figure 1:
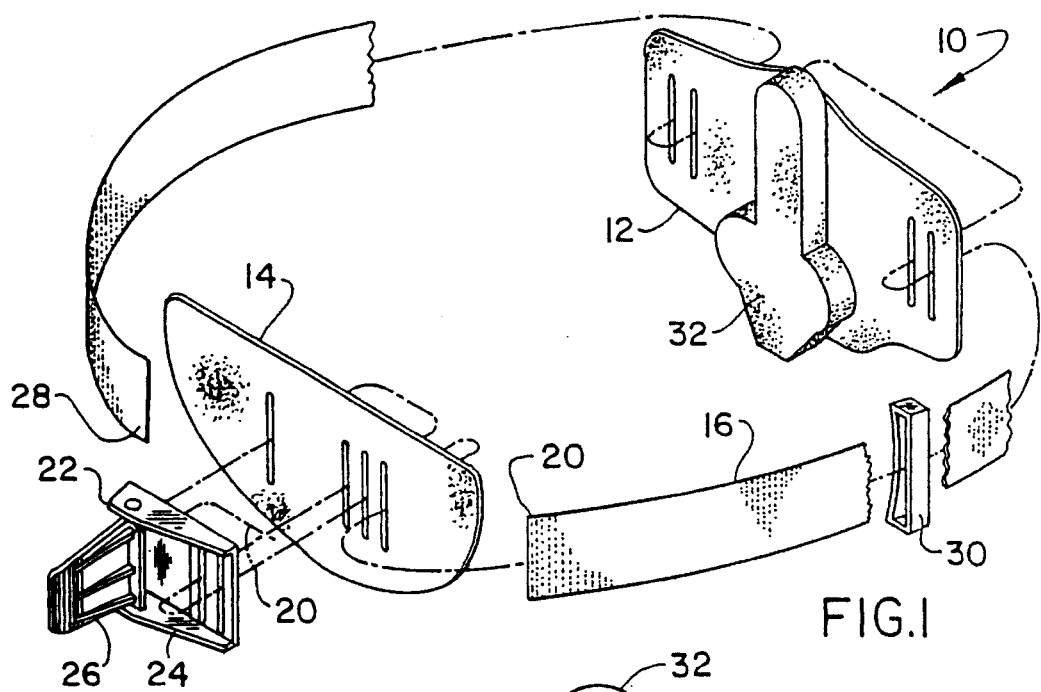
FIG. 1 is an exploded perspective view of the within back brace.
Figure 6:
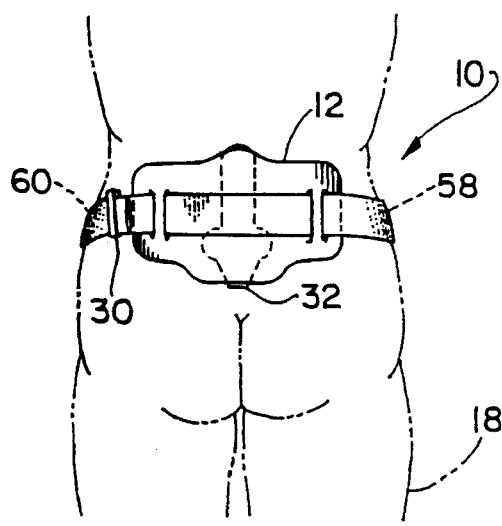
FIGS. 6 and 7 are respectively front and rear perspective views of the back brace during use.
Figure 7:
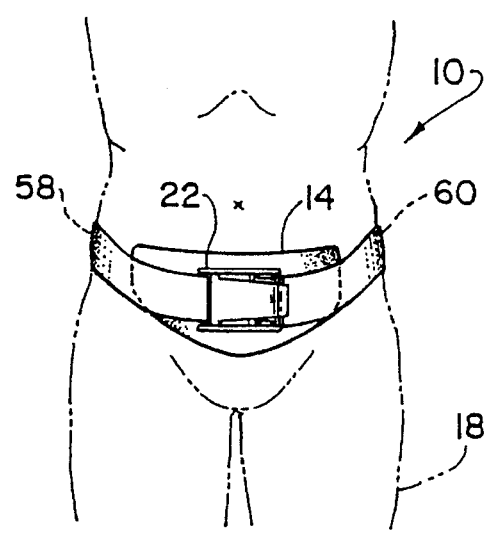
Figure 8:
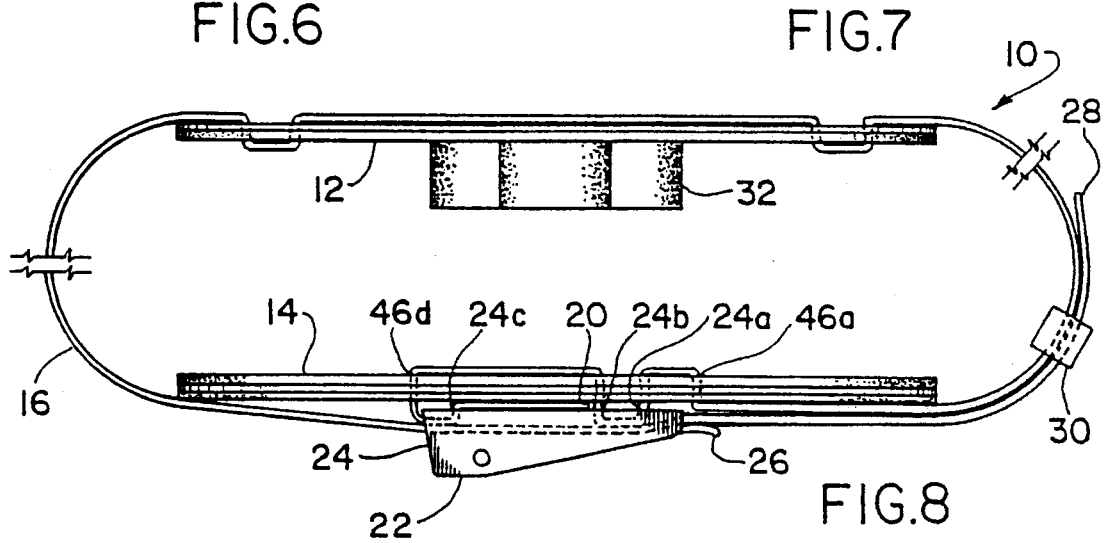
FIG. 8 is an isolated plan view of the back brace in assembled condition.

As may best be appreciated from FIG. 1, the within inventive back brace, generally designated 10, is of the type comprised of a back panel 12 and a cooperating front panel 14, respectively positioned against the user's back (FIG. 6) and stomach (FIG. 7), while supported on a belt 16 having an operative encircling relation about the waist of the user 18, as best illustrated in FIG. 8.

Figure 9:
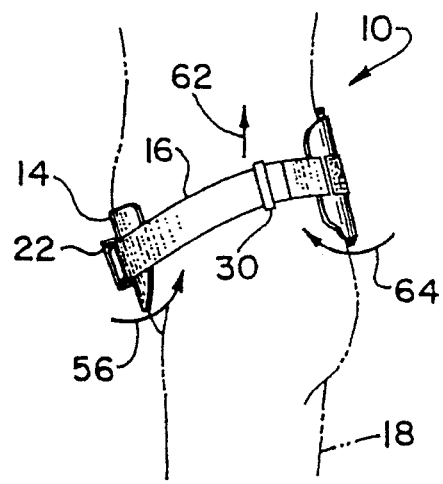
FIG. 9 is a side elevational view of the back brace including a schematic of the forces generated and movements of the component parts during use.

As shown in FIG. 8 in relation to a front positioned buckle 22, an end 20 of belt 16 is, after its attachment to buckle 22, threaded through a slot, as at 24C, about a buckle end in a reverse direction, as at 46d, in underlying relation to the front panel 14 and then through three encountered front panel slots, as at 24b, 24a, 46a, positioning the belt in overlying relation to the front panel 12, and the threading continuing in a counterclockwise direction from front panel 12 through back panel slots 38 (FIG. 2), as noted by the dash-dot reference line in FIG. 1, and terminating in a belt opposite end length portion 28 clamped beneath a pivotally mounted buckle latch 26, the end of the clamped length portion 28 being confined against flapping by a keeper 30, as noted in FIG. 9.

Figures 4, 5:
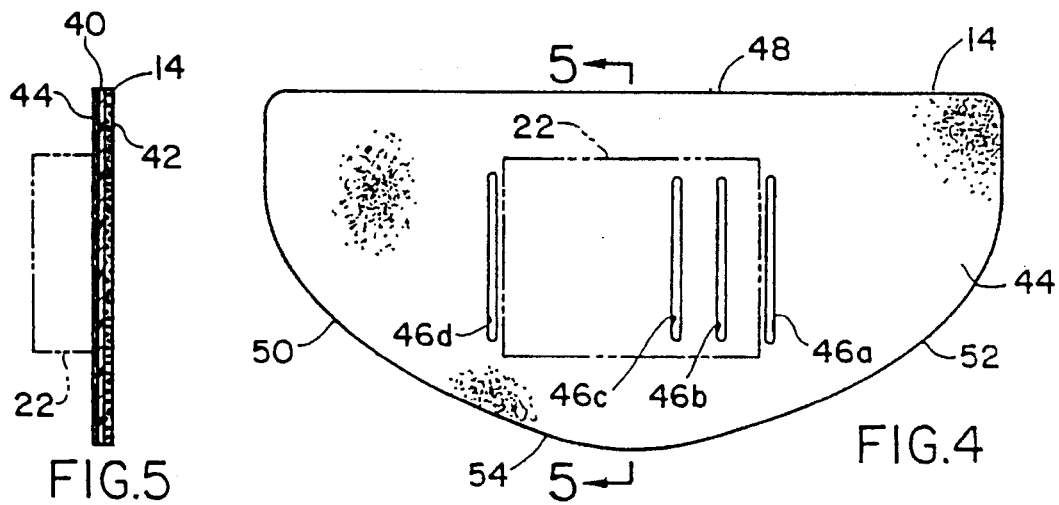
FIG. 4 is a view similar to FIG. 2, but of the front panel of the back brace.
FIG. 5 is a cross sectional view as taken along line 5—5 of FIG. 4.

Thus far what has been described is generally known in the prior art. What is a significant prior art departure is the belt-tightening functioning of the buckle 22 in relation to downwardly converging opposite sides 50 and 52 of front panel 14, as best shown in FIG. 4. More particularly, and underlying the present invention is the recognition that in tightening belt 16 through buckle 22 the initial and terminal length portions of the belt are in overlying and crossing relation to the front panel angular edges 50 and 52 and the response to the tightening forces is to set off a chain of movements initiated by a camming or lifting movement 56 in front panel 14 producing a reaction or countering lifting movement 64 in back panel 12 and overall ascending movement 62 in the back brace 10, as noted in FIG. 9. The respective lifting forces 56 and 64 have been found in practice to apply comfortable pressure against the sacrum of the user, as well as providing other therapeutic benefits for the user.

The within inventive back brace 10 should be readily understood as to both its construction and operating mode from the preceding description. However, for completeness' sake a further brief description thereof is provided.

Figures 2, 3:
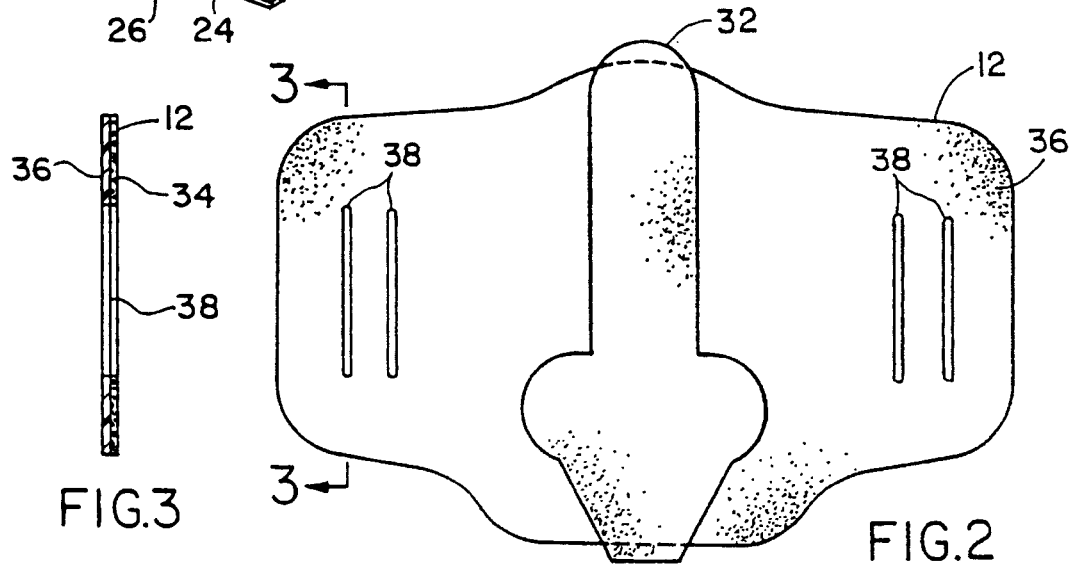
FIG. 2 is an isolated elevational view, as seen from the front, of the back panel of the back brace.
FIG. 3 is a cross sectional view as taken along line 3—3 of FIG. 2.

In a preferred embodiment, back panel 12 has a medial shaped member 32 of foam construction material 36 adhesively secured to a ply 34 of plastic construction material, best illustrated in the cross section in FIG. 3. Front panel 14, as best illustrated in cross section and elevation in respective FIGS. 5 and 4, consists of a plastic ply 40 to opposite sides of which are appropriately adhered or otherwise attached a foam layer 42 and felt layer 44, to provide a stomach-engaging surface between a top edge 48 and bottom edge 54. In use, the length portions of the supporting belt 16 extending between the panels 12 and 14 are in turn supported on the hip bones, i.e. crests of the ilium 58, 60 (FIGS. 6, 7) which is a favorable starting position for the ascending movement 62 of the back brace 10.

The remaining major buckle component 22 is comprised of a base member 24 to which is pivotally mounted a latch 26 and is of a readily commercially available type, such as model C8-2 available from American Cord and Webbing of New York, N.Y.

While the back brace and the method of use thereof herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A method of adjusting incident to applying pressure against a user's back, a back brace of a type having a back panel, a front panel, and a waist-encircling belt, said back brace-adjusting method comprising the steps of positioning said back panel in an operative position adjacent a selected location of said user's back, positioning said front panel characterized by opposite side edges angularly downwardly converging towards each other to correspondingly present in a semi-circular configuration panel-camming surfaces along a bottom edge thereof in an operative position adjacent a selected location of said user's stomach, positioning opposite length portions of said waist-encircling belt extending in opposite directions from an attachment to said back panel in crossing relation to said panel-camming surfaces of said front panel, holding, by initial tightening said waist-encircling belt said back and front panels in contact with said user at said selected locations, and urging said front panel in an ascending path of movement by subsequent tightening of said waist-encircling belt incident to the camming thereof at said crossing contact of said belt length portions and said panel-camming surfaces of said front panel, whereby there is a corresponding ascending movement in said back panel resulting in back-supporting pressure being applied to said user's back.

\* \* \* \* \*